United States Patent [19]

Hudson

[11] 4,021,490

[45] May 3, 1977

[54] PROCESS FOR PRODUCTION OF PHENOL AND CYCLOHEXANONE

[75] Inventor: Paul S. Hudson, Bartlesville, Okla.

[73] Assignee: Phillips Petroleum Company, Bartlesville, Okla.

[22] Filed: Oct. 14, 1975

[21] Appl. No.: 621,897

[52] U.S. Cl. .............................. 260/586 R; 203/58; 260/586 R; 260/621 A; 260/621 C
[51] Int. Cl.² .................. C07C 45/02; C07C 45/24; C07C 37/08; C07C 37/34
[58] Field of Search ....... 260/586 R, 586 P, 621 A, 260/621 C; 203/58

[56] References Cited

UNITED STATES PATENTS

| | | | |
|---|---|---|---|
| 2,360,859 | 10/1944 | Evans et al. | 203/58 |
| 2,762,760 | 9/1956 | Walker | 260/621 A |
| 2,950,320 | 8/1960 | Vandenburg | 260/621 C |

*Primary Examiner*—Norman Morganstern

[57] ABSTRACT

Benzene is converted by reductive alkylation to cyclohexylbenzene; cyclohexylbenzene by oxidation and cleavage is converted into a mixture of cyclohexylbenzene, phenol and cyclohexanone; after removal of cyclohexylbenzene from this mixture, the remaining mixture consisting essentially of phenol and cyclohexanone is effectively separated into its components by extractive distillation with a sulfolane.

14 Claims, 1 Drawing Figure

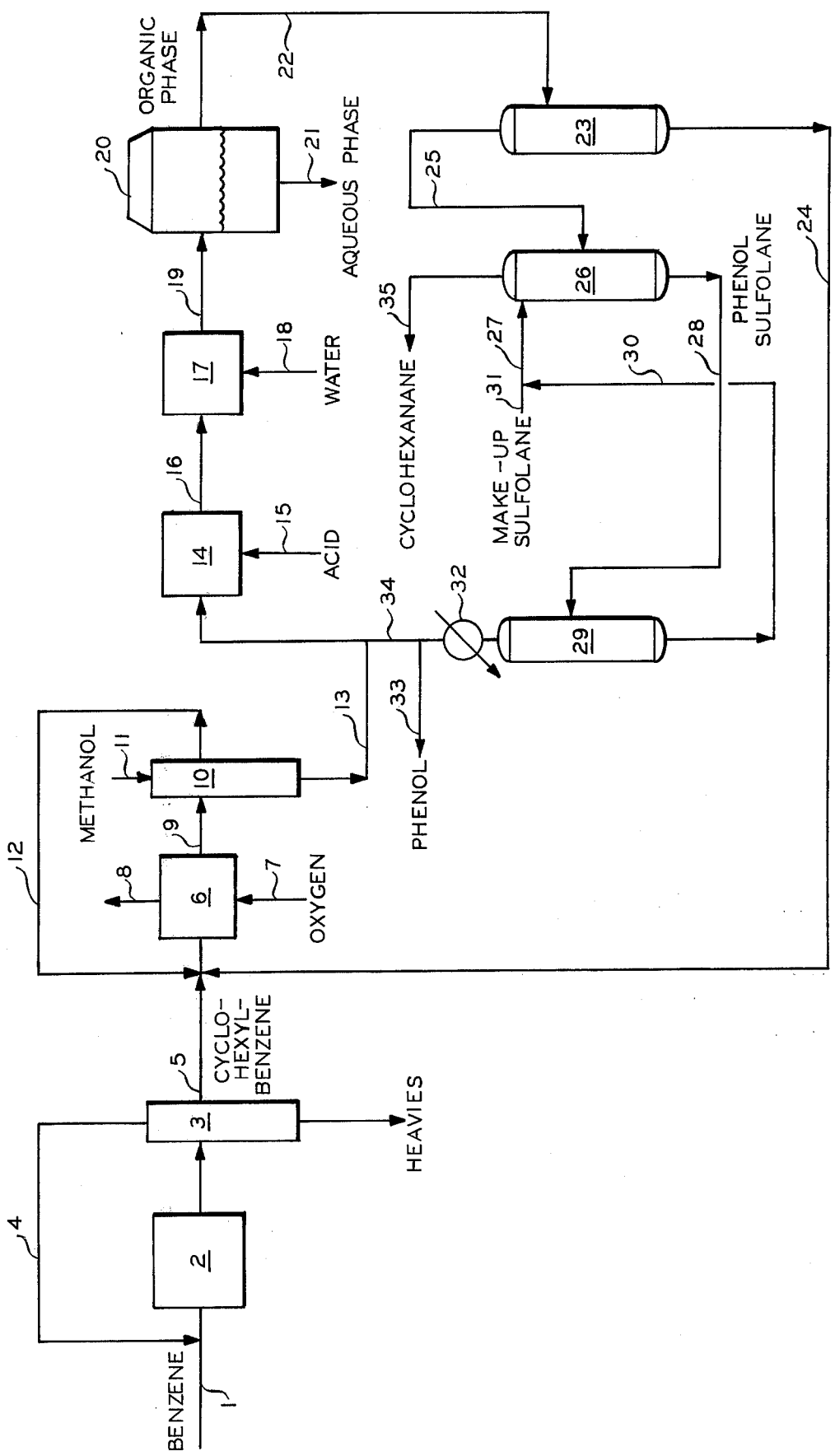

PROCESS FOR PRODUCTION OF PHENOL AND CYCLOHEXANONE

This invention relates to the production of phenol and cyclohexanone. In one of its more specific aspects, the invention relates to a process for the separation of a mixture of phenol and cyclohexanone.

BACKGROUND OF THE INVENTION

It is known in the art that benzene can be converted into phenol by a reductive alkylation step forming cyclohexylbenzene followed by oxidation and cleavage steps resulting essentially in phenol and cyclohexanone. Phenol and cyclohexanone, however, form an azeotropic mixture. Therefore, a mixture consisting essentially of cyclohexanone and phenol cannot be separated by simple distillation. In order to produce the pure components, it would therefore be desirable to have a process available by which this mixture of phenol and cyclohexanone can effectively be separated.

THE INVENTION

It is, therefore, one object of this invention to provide a process for separating a mixture of phenol and cyclohexanone into its constituents.

Another object of this invention is to provide a process for the production of phenol and cyclohexanone from benzene.

A still further object of this invention is to improve a process for the production of phenol and cyclohexanone, in which process phenol is used as a diluent or solvent in a step in which cyclohexylbenzene hydroperoxide is decomposed into phenol and cyclohexanone, by producing pure phenol which can at least partially be recycled into this step.

These and other features, advantages, embodiments and details of this invention will become apparent to those skilled in the art from the following detailed description of the invention, the appended claims and the drawing which shows a schematic flow diagram for a process for making phenol and cyclohexanone.

In accordance with this invention, I have now found that a mixture consisting essentially of phenol and cyclohexanone can be effectively separated by extractively distilling this mixture with a sulfolane as a solvent.

More specifically, I have found that phenol and cyclohexanone form an azeotrope of about 72 mol percent phenol and 28 mol percent cyclohexanone, said azeotrope boiling at 164.5° C at atmospheric pressure, and that this azeotrope can effectively be separated by extractively distilling it with a sulfolane into a gaseous overhead stream of cyclohexanone and a liquid bottom stream consisting essentially of a mixture of the sulfolane and phenol. The liquid bottom stream is readily separated in accordance with a preferred embodiment of this invention by regular distillation into an overhead phenol stream and liquid sulfolane bottom stream.

The preferred group of sulfolanes that can be used in accordance with this invention is defined by having the general formula

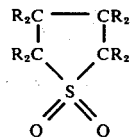

in which the radicals R, which can be the same or different, are selected from the group of hydrogen, lower alkyl radicals having 1 to 6 carbon atoms and phenyl. Preferably the radicals R are selected from the group consisting of hydrogen and methyl. The presently most preferred group of sulfolanes consists of unsubstituted sulfolane, 3-methyl sulfolane, and mixtures thereof.

Further examples are contained in the following group of substituted sulfolanes which can be used as the extractive solvent for the separation step of this invention: 2-methyl sulfolane, 3-methyl sulfolane, 2-ethyl sulfolane, 2,5-dimethyl sulfolane, 2,4-dimethyl sulfolane, 2,3-dimethyl sulfolane, 2,2-dimethyl sulfolane, 3,4-dimethyl sulfolane, 3-ethyl sulfolane, 2-propyl sulfolane, 2-ethyl sulfolane, 2-methyl-5-ethyl sulfolane, 2-isopropyl sulfolane, 2-ethyl-3-methyl sulfolane, 2-methyl-2-ethyl sulfolane, 2,2,5-trimethyl sulfolane, 2,3,5-trimethyl sulfolane, 3,4,5-trimethyl sulfolane, 2,2,4-trimethyl sulfolane, 2-methyl-3-ethyl sulfolane, 3-isopropyl sulfolane, 2-methyl-5-propyl sulfolane, 2,5-dimethyl sulfolane, 2-propyl-4-methyl sulfolane, 2,3-dimethyl-5-ethyl sulfolane, 2,4-dimethyl-5-ethyl sulfolane, 2-methyl-5-isopropyl sulfolane, 3-methyl-5-isopropyl sulfolane, 2,3,4,5-tetramethyl sulfolane, 2,2,4,5-tetramethyl sulfolane, 2,2,5,5-tetramethyl sulfolane, 2,2-dimethyl-4-ethyl sulfolane, 3-butyl sulfolane, 2,3-dimethyl-5-propyl sulfolane, 2-methyl-5-isobutyl sulfolane, 2,5-diethyl-3-methyl sulfolane, 2-isobutyl-4-methyl sulfolane, 2,2-dimethyl-5-isopropyl sulfolane, 2,3-dimethyl-5-isopropyl sulfolane, 3-ethyl-2-propyl sulfolane, 2,5-dimethyl-5-ethyl sulfolane, 2-tertiary butyl-4-methyl sulfolane, 2-hexyl sulfolane, 2-ethyl-3-methyl-5-propyl sulfolane, 2,3-dimethyl-5-butyl sulfolane, 2-methyl-5-isobutyl sulfolane, 2-methyl-4-ethyl-5-propyl sulfolane, 2-isopentyl-3-methyl sulfolane, 2,2-dimethyl-5-isobutyl sulfolane, 2,3-dimethyl-5isobutyl sulfolane, 2-isopropyl-4-methyl-5-ethyl sulfolane, 2,5-dimethyl-2,5-diethyl sulfolane, 2,5-dimethyl-3,4-diethyl sulfolane, 3-methyl-5-hexyl sulfolane, 2-methyl-2-hexyl sulfolane, 2,5-dipropyl-3-methyl sulfolane, 2-isopropyl-3-methyl-5-propyl sulfolane, 2-ethyl-3-methyl-5-isobutyl sulfolane, 2,5-diisopropyl-3-methyl sulfolane, 2,2,4-trimethyl-5-isobutyl sulfolane, 3-heptyl sulfolane, 3,4-ditertiary butyl sulfolane, 2-phenyl sulfolane, 3-phenyl sulfolane, 2-phenyl-5-methyl sulfolane, 3-phenyl-5-methyl sulfolane, 2-phenyl-5-ethyl sulfolane, 2-phenyl-3,4-dimethyl sulfolane, and 2-phenyl-5-propyl sulfolane.

The quantity in which the sulfolane is employed is not critical. However, the more sulfolane used per unit of phenol, the more effective the extractive distillation becomes. The quantity used depends to a certain extent upon the number of trays (or the theoretical number of separation steps in the distillation column). Mol ratios of sulfolane to phenol circulated in the distillation unit in the range of 2:1 to 15:1 are presently preferred.

The extractive distillation can be carried out under various pressures. It is presently preferred, though, to carry out the extractive distillation under atmospheric pressure. In this case the temperature range for the extractive distillation in the column is about 110° to 185° C when unsubstituted sulfolane is used and 155° to 185° C in case when 3-methyl sulfolane is used.

It is within the scope of this invention to first subject the phenol/cyclohexanone mixture to a regular distillation step to form a first stream of an azeotropic mixture of phenol and cyclohexanone and a second stream of one of the components; then only the azeotropic mixture of phenol and cyclolhexanone is subjected to the extractive distillation of this invention. It is presently preferred, however, to subject the mixture of phenol and cyclohexanone as it is produced to the extractive distillation step with the sulfolane.

In accordance with a further embodiment of this invention, there is provided an improved process for the production of phenol and cyclohexanone which comprises converting benzene in the presence of a reductive alkylation catalyst to cyclohexylbenzene, oxidizing said cyclohexylbenzene produced to obtain a mixture of cyclohexylbenzene, phenol and cyclohexanone, separating the resulting mixture of cyclohexylbenzene, phenol and cyclohexanone to obtain a mixture of phenol and cyclohexanone and a stream of cyclohexylbenzene, thereafter extractively distilling the first mixture of phenol and cyclohexanone with a sulfolane as the extractive solvent whereby there is obtained a stream of cyclohexanone and a second mixture of phenol and sulfolane.

The step of converting benzene into cyclohexylbenzene by a reductive alkylation is preferably carried out in the presence of a reductive alkylation catalyst comprising one or more transition metals and one or more Friedel-Crafts promoters. The presently preferred group of transition metals are ruthenium and nickel. The presently preferred Friedel-Crafts promoters are HF, $AlCl_3$ and $BF_3$ treated silica-alumina. This reductive alkylation step as such is known from the U.S. Pat. No. 3,829,516.

The oxidation of the cyclohexylbenzene is preferably carried out by contacting cyclohexylbenzene with oxygen at elevated temperatures. The usually employed range for the oxidation temperature is about 60 to about 160° C. This oxidation results in a mixture of cyclohexylbenzene and cyclohexylbenzene hydroperoxide.

The mixture obtained by the oxidation of the cyclohexylbenzene is preferably extracted with a solvent such as methanol. The extract consists essentially of methanol and cyclohexylbenzene hydroperoxide, whereas the remainder of the extraction step consists essentially of cyclohexylbenzene, which is recycled to the oxidation step.

The extract consisting essentially of methanol and cyclohexylbenzene hydroperoxide is diluted with phenol and thereafter is treated with a strong acid, such as sulfuric acid, resulting in a mixture consisting essentially of methanol, phenol, cyclohexanone, and cyclohexylbenzene.

The acid that can be used for this cleavage or hydroperoxide decomposition step is preferably selected from the group consisting of acetic acid, sulfuric acid, p-toluene sulfonic acid and trichloroacetic acid. It is presently most preferred to carry out the cleavage or hydroperoxide decomposition step in the presence of methanol and phenol. This mixture is treated with water and the resultant water-methanol phase separated from the organic phase. The organic phase of this mixture consists essentially of cyclohexylbenzene, phenol and cyclohexanone. This organic phase is thereafter fractionally distilled to result in a liquid bottom stream consisting essentially of cyclohexylbenzene and a gaseous overhead stream consisting essentially of phenol and cyclohexanone.

The gaseous overhead stream of phenol and cyclohexanone thereafter is extractively distilled utilizing sulfolane as explained above in detail.

The liquid bottom stream of phenol and sulfolane obtained is separated by regular distillation resulting in a stream of phenol and a stream of sulfolane.

In this overall process to produce phenol and cyclohexanone, it is presently preferred to recirculate one or more of the following streams partially or in their entirety. Thus, in accordance with one embodiment of this invention, the cyclohexylbenzene stream obtained during the fractionation of the organic phase described above is recirculated into the oxidation step in which the cyclohexylbenzene is oxidized to form cyclohexylbenzene hydroperoxide. In accordance with a further embodiment, the sulfolane obtained during the distillation of the sulfolane/phenol mixture is reintroduced into the extractive distillation step in which the mixture of phenol and cyclohexanone are extractively distilled using the sulfolane as the extractive solvent. In accordance with another embodiment, finally the phenol stream obtained by the distillation of the sulfolane/phenol mixture is partially reintroduced into the cleavage step in which the cyclohexylbenzene hydroperoxide is converted into phenol and cyclohexanone in the presence of a strong acid and in the presence of phenol.

Phenol and cyclohexanone are ultimately recovered as the product of the process. In accordance with still another embodiment of this invention, the cyclohexanone recovered is converted into phenol by conventional steps, which as such are well known in the art. This overall process results in phenol as the sole product of the process.

DESCRIPTION OF THE DRAWING

As shown in the drawing, which is a schematic flow diagram of an overall process to produce phenol and cyclohexanone from benzene, benzene is introduced via line 1 into a reactor 2 containing a reductive alkylation catalyst.

The reaction product of this step is separated in a separating unit 3. Unreacted benzene and entrained catalyst is reintroduced into the reactor 2 via line 4. A stream of cyclohexylbenzene is passed to oxidation reactor 6. In this oxidation reactor, the cyclohexylbenzene is contacted with oxygen which is introduced via line 7. The unused oxygen leaves the reactor 6 via line 8. The reaction mixture of the oxidation step leaves the reactor via line 9 and is introduced into a separating unit 10. In this separating unit, the reaction product of the oxidation step is contacted with methanol, which is introduced into this separating unit 10 via line 11. The nonextracted materials are reintroduced from said separating unit 10 via line 12 into the oxidation reactor 6. The extract from the separating unit 10 is introduced via line 13 into a cleavage reactor 14. In this cleavage reactor the extract comprising cyclohexylbenzene hydroperoxide and methanol is contacted with a strong acid which is introduced into the cleavage reactor 14 via line 15. Preferably phenol, as well as methanol, are present in the cleavage reactor 14.

The reaction product of the cleavage reactor 14 is passed via a line 16 to a mixing contactor 17 in which this reaction product is mixed with water, which is introduced via line 18 into this mixing unit 17. The two-phase mixture obtained is passed via line 19 into a settler 20. The aqueous phase is removed from settler via line 21. The organic phase comprising cyclohexylbenzene, phenol, and cyclohexanone is passed via line 22 into a fractionation column 23. A liquid bottom stream consisting essentially of cyclohexylbenzene is withdrawn from this fractionation column 23 via line 24 and is reintroduced into the oxidation reactor 6.

An overhead gaseous stream consisting essentially of phenol and cyclohexanone is passed from said fractionator 23 via line 25 to an extractive distillation column 26. Sulfolane is being introduced into this extractive distillation unit 26 via line 27.

A liquid bottom stream consisting essentially of phenol and sulfolane is withdrawn from the extractive distillation column 26 via line 28 and passed to a distillation column 29. A gaseous overhead stream consisting essentially of cyclohexanone is withdrawn from said extractive distillation column 26 as one of the products of the process.

In the distillation column 29, the phenol/sulfolane mixture is separated into a sulfolane stream which is reintroduced into the extractive distillation unit 26 via lines 30 and 27. Makeup sulfolane is added via line 31 if necessary.

From the distillation column 29, a gaseous overhead stream of phenol is withdrawn, condensed in condenser 32 and partially reintroduced into the cleavage reactor 14. The rest of the phenol is recovered via line 33 as the other product of the process.

The invention will be still more fully understood from the following examples illustrating further preferred embodiments of this invention. The examples are not intended to limit the scope of this invention.

EXAMPLE I

Phenol/Cyclohexanone Azeotrope

This example is provided to show the formation of a phenol/cyclohexanone azeotrope during the distillation of a mixture of phenol and cyclohexanone. The equipment used in the Examples I, II and III was a packed fractionating column of 50 cm length and 25 mm internal diameter, corresponding to approximately 5 theoretical fractionation steps. The column was further equipped with a 200 ml kettle and a distillation head.

A mixture of 54 g of phenol and 52 g of cyclohexanone was placed in the kettle. The distillation then was carried out at atmospheric pressure. The results of this distillation are shown in the following Table I.

TABLE I

| Overhead Cut | Boiling Range, ° C | Distillate, ml. | Distillate Composition, wt. % | |
|---|---|---|---|---|
| | | | Phenol | Cyclohexanone |
| 1 | 60–152 | 10 | 0 | 100 |
| 2 | 152–165 | 10 | 0 | 100 |
| 3 | 165–176 | 10 | 26.4 | 73.6 |
| 4 | 176 | 10 | 57.6 | 42.4 |
| 5 | 176–182 | 10 | 64.2 | 35.8 |
| 6 | 182 | 10 | 68.3 | 31.7 |
| 7 | 182 | 10 | 70.8 | 29.2 |
| 8 | 182 | 10 | 71.3 | 28.7 |
| 9 | 182 | 10 | 72.6 | 27.4 |
| 10 | Kettle | 10 | | |

From the results shown above, it can be clearly seen that a further separation of the phenol/cyclohexanone was not possible, but that an azeotropic mixture of phenol and cyclohexanone formed as obtained in cuts 7, 8, and 9.

EXAMPLE II

Extractive Distillation of a Phenol/Cyclohexanone Mixture

The same equipment as in Example I was used. A mixture of 25 g phenol and 25 g cyclohexanone together with 100 g unsubstituted sulfolane was placed in the kettle. The distillation of this three component mixture was then carried out at atmospheric pressure. The result obtained during this distillation are shown in the following Table II.

TABLE II

| Overhead Cut | Boiling Range ° C | Distillate, ml. | Distillate Composition Sulfolane-free basis, wt. % | |
|---|---|---|---|---|
| | | | Phenol | Cyclohexanone |
| 1 | 115–151 | 2 | 0 | 100 |
| 2 | 151–160 | 17 | 0 | 100 |
| 3 | 160–182 | 3 | 23.3 | 76.7 |
| 4 | 182 | 20 85% overhead | 86.4 | 13.6 |

From the results shown above, it can be seen that an effective separation of phenol and cyclohexanone was possible, as a phenol product richer than the azeotrope was obtained. The weight percentages shown in this Table II are based on the mixture of phenol and cyclohexanone as 100 percent, the sulfolane is not included in these figures. By using a more efficient fractionating column, for instance, a fractionating column with 15 or 20 theoretical plates pure phenol can be obtained in this process.

EXAMPLE III

Extractive Distillation of a Phenol/Cyclohexanone Mixture with 3-Methyl Sulfolane Into the same equipment as used in Example I, a mixture of 35 g phenol, 15 g cyclohexanone and 100 ml 3-methyl sulfolane was placed. The distillation was carried out at atmospheric pressure. The results of this distillation are shown in the following Table III.

TABLE III

| Overhead Cut | Boiling Range, ° C | Distillate, ml. | Distillate Composition, wt. % | |
|---|---|---|---|---|
| | | | Phenol | Cyclohexanone |
| 1 | 156–160 | 2 | 2.2 | 97.8 |
| 2 | 160–176 | 4 | 2.9 | 97.1 |
| 3 | 176–182 | 3 | 11.8 | 88.2 |
| 4 | 182 | 25 | 78.4 | 21.6 |
| 5 | 182 | 4 | 94.2 | 5.8 |

The results shown above again indicate that the phenol/cyclohexanone mixture was very effectively separated by using 3-methyl sulfolane as the extractive solvent. A still better separation would have been possible with a more efficient fractionating column.

The following is a calculated example for the overall process to produce phenol and cyclohexanone.

EXAMPLE IV

Production of Phenol and Cyclohexanone from Benzene

Referring to the lone FIGURE illustrating the production of phenol and cyclohexanone from benzene, stream 1 amounting to 1000 pounds per hour of makeup benzene is passed together with 8000 pounds per hour of recycle benzene into reductive alkylation reactor 2. A catalyst of 0.5 wt. % ruthenium and 0.25 wt. % nickel deposited on silica alumina and designated as Filtrol Grade 71 tablets is used in reactor 2 at a temperature of 150° C and a LHSV (liquid hourly space velocity) of 6. Excess hydrogen is flowed through the reactor at a pressure of 500 psig; about 10 percent of the benzene is converted to cyclohexylbenzene under these conditions. Small amounts of lighter and heavier compounds are also formed and are removed from the reaction effluent by fractionation steps not shown in the FIGURE. Reaction effluent is then passed to fractionator 3, wherein unreacted benzene at the rate of 8000 pounds per hour is recovered overhead and recycled to reactor 2. Heavy by-products are removed from the bottom of fractionator 3 at the rate of about 100 pounds per hour. Product cyclohexylbenzene is removed from the center of fractionator 3 at the rate of 900 pounds per hour and passed together with 200 pounds per hour of recycle cyclohexylbenzene from pipe 24 to oxidation reactor 6. The cyclohexylbenzene is contacted with oxygen at a pressure of about 100 psig in reactor 6 at a temperature of 120° C. Oxygen enters via pipe 7 at the rate of 1000 pounds per hour and the excess exits via pipe 8. Cyclohexylbenzene conversion to hydroperoxide is 20% and selectivity to hydroperoxide is 88%. Effluent from reactor 6 passes via pipe 9 to methanol scrubber 10, wherein methanol at the rate of 1000 pounds per hour is passed into the top of scrubber 10 via pipe 11. The methanol selectively dissolves the hydroperoxide and the resultant solution is removed from the bottom of scrubber 10 via pipe 13. Undissolved cyclohexylbenzene is removed from the top and recycled via pipe 12 at the rate of 5000 pounds per hour to oxidation reactor 6. Stream 13, now consisting of 1000 pounds per hour of methanol, 200 pounds per hour of cyclohexylbenzene, and 1000 pounds of hydroperoxide, is mixed with 1000 pounds per hour of phenol via pipe 34 and passed to hydroperoxide cleavage reactor 14. Sulfuric acid is added to reactor 14 via pipe 15 at the rate of 10 pounds per hour to hasten the decomposition of the hydroperoxide into phenol and cyclohexanone. Temperature in reactor 14 is about 45° C and residence time about 2 hours. Effluent from reactor 14 consists of 1000 pounds per hour of methanol, about 1450 pounds per hour of phenol, about 450 pounds per hour of cyclohexanone, about 200 pounds per hour of cyclohexylbenzene and about 100 pounds per hour of undecomposed hydroperoxide and is passed via pipe 16 to contactor 17, to which water is added at the rate of 5000 pounds per hour. Effluent from contactor 17 is passed into phase separator 20, wherein the mixture separates into an organic phase consisting of cyclohexylbenzene, phenol, and cyclohexanone, and an aqueous phase consisting of water, methanol, and hydroperoxide. The aqueous phase is removed from contactor 20 via pipe 21 and after removal of most of the water and methanol, by means not shown, is recycled to reactor 14. The water and methanol are also separated and recycled by steps not shown.

The organic phase, consisting of 200 pounds per hour of cyclohexylbenzene, 1450 pounds per hour of phenol, and 450 pounds per hour of cyclohexanone, is passed via pipe 22 to fractionator 23, wherein cyclohexylbenzene is removed as bottoms product via pipe 24 and a mixture of phenol and cyclohexanone removed overhead via pipe 25. Fractionator 23 contains about 100 theoretical fractionation steps or about 150 actual contacting trays. It operates under about 25 psig pressure and with top and bottom temperatures of about 180° and 250° C, respectively. Overhead from fractionator 23 is condensed and about 90% of the condensate liquid returned to the top of the fractionator as reflux (not shown in the FIGURE).

The mixture of phenol and cyclohexanone in stream 25 is passed to the center of extractive distillation column 26. Sulfolane in the amount of 10,000 pounds per hour is passed as selective solvent to the top of column 26 via pipe 27. Column 26 contains about 25 theoretical separation steps or about 50 actual fractionation steps. Substantially pure cyclohexanone is recovered overhead via pipe 35 in the amount of 450 pounds per hour. The slight amount of sulfolane present in the cylcohexanone product may be separated by a water wash by conventional means not shown. Column 26 operates at 25 psig and with top and bottom temperatures of 185° and 250° C, respectively.

A mixture of sulfolane and phenol is withdrawn from the bottom of column 26 and passed to stripper-fractionator 29, which operates as an ordinary fractionator to separate sulfolane from cyclohexanone. Fractionator 29 contains about 50 actual fractionation trays, operates at 25 psig, and has top and bottom temperatures of 185° C and 250° C, respectively. Phenol is recovered as overhead product from fractionator 29, condensed in cooler 32, and about 50% of the condensate returned to the fractionator as reflux. The remaining overhead condensate in the amount of 1450 pounds per hour of phenol is divided with 450 pounds per hour taken as product via pipe 33, and the remaining 1000 pounds recycled to the hydroperoxide decomposition reactor 14. Sulfolane in the amount of 10,000 pounds per hour is recovered as bottoms product from fractionator 29 and recycled to extractive distillation column 26 via pipe 30. Make-up sulfolane is added via pipe 31 in response to loses, leaks, etc.

The preceeding example is, of course, idealized in that impurities in the various streams have been neglected. This does not detract from the illustration of the overall process for converting benzene into phenol and cyclohexanone.

Reasonable variations and modifications, which would be apparent to those skilled in the art, can be made in this invention without departing from the spirit and scope thereof.

I claim:

1. A process for separation of a mixture of phenol and cyclohexanone which comprises extractively distilling said mixture of phenol and cyclohexanone in the presence of a sulfolane having the formula

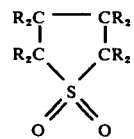

in which R is hydrogen or an alkyl radical having 1 to 6 carbon atoms or phenyl as the extractive solvent to result in an overhead stream of cyclohexanone and a bottom stream consisting of essentially of a mixture of sulfolane and phenol.

2. A process in accordance with claim 1 wherein said bottom stream of the mixture of sulfolane and phenol is separated into the ingredients thereof by fractionation of said bottom stream.

3. A process in accordance with claim 1 wherein said sulfolane is selected from the group consisting of unsubstituted sulfolane, 3-methylsulfolane, and mixtures thereof.

4. A process in accordance with claim 1 wherein said sulfolane is used in the extractive distillation step in a molar ratio of sulfolane to phenol in the range of 2:1 to 15:1.

5. A process in accordance with claim 1 wherein said extractive distillation is carried out under atmospheric pressure.

6. A process for the production of phenol and cyclohexanone which comprises
   a. converting benzene in the presence of a reductive alkylation catalyst to cyclohexylbenzene,
   b. contacting said cyclohexylbenzene in an oxidation step with oxygen or an oxygen-containing oxidizing compound and thereby at least partially converting said cyclohexylbenzene into cyclohexylbenzene hydroperoxide.
   c. contacting said cyclohexylbenzene hydroperoxide in a cleavage step with a strong acid and thereby at least partially converting it into a mixture comprising phenol, cyclohexanone and cyclohexylbenzene,
   d. separating cyclohexylbenzene in a separation step from said mixture comprising phenol, cyclohexanone and cyclohexylbenzene to result in a stream consisting essentially of phenol and cyclohexanone,
   e. extractively distilling said stream of phenol and cyclohexanone in the presence of a sulfolane having the general formula

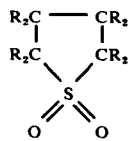

wherein the radicals R, which can be the same or different, are individually selected from the group consisting of hydrogen, lower alkyl radicals having 1 to 6 carbon atoms and phenyl as the extractive solvent in an extraction step to result in a stream consisting essentially of cyclohexanone and another stream consisting essentially of a mixture of phenol and sulfolane.

7. A process in accordance with claim 6 wherein the reaction mixture obtained by the oxidation step is extracted with methanol to result in an extract consisting essentially of methanol and cyclohexylbenzene hydroperoxide and wherein said extract is then further treated by subjecting it to said cleavage step.

8. A process in accordance with claim 7 wherein the reaction product of said cleavage step consisting essentially of methanol, phenol, cyclohexanone and cyclohexylbenzene is mixed with water, wherein the resulting mixture obtained is phase separated into an aqueous phase and an organic phase and wherein said organic phase is then subjected to said separation step.

9. A process in accordance with claim 6 wherein said stream of mixture of phenol and sulfolane is fractionated to result in a stream of sulfolane and a stream of phenol.

10. A process in accordance with claim 6 wherein said sulfolane is selected from the group consisting of unsubstituted sulfolane and 3-methyl sulfolane.

11. A process in accordance with claim 6 wherein said sulfolane is used during said extraction step in a molar ratio of sulfolane to phenol in the range of 2:1 to 15:1.

12. A process in accordance with claim 6 wherein said extractive distillation is carried out under atmospheric pressure.

13. A process in accordance with claim 6 wherein said cleavage step is carried out in the presence of phenol and methanol wherein said stream of a mixture of phenol and sulfolane is separated into a phenol stream and a sulfolane stream, wherein part of said phenol stream is reintroduced into said cleavage step and wherein said sulfolane stream is reintroduced into said extraction step.

14. A process in accordancae with claim 6 wherein said cyclohexylbenzene separated from said mixture comprising cyclohexylbenzene, phenol and cyclohexanone during said separation step is reintroduced into said oxidation step.

* * * * *

Disclaimer 4,021,490.—*Paul S. Hudson*, Bartlesville, Okla. PROCESS FOR PRODUCTION OF PHENOL AND CYCLOHEXANONE. Patent dated May 3, 1977. Disclaimer filed Aug. 14, 1978, by the assignee, *Phillips Petroleum Company*.

Hereby enters this disclaimer to claim 13 of said patent.

[*Official Gazette October 17, 1978.*]